United States Patent [19]

Fabian et al.

[11] Patent Number: 5,107,862

[45] Date of Patent: * Apr. 28, 1992

[54] SURGICAL IMPLEMENT DETECTOR UTILIZING A POWERED MARKER

[76] Inventors: Carl E. Fabian, 577 NE. 96th St., Miami Shores, Fla. 33138; Philip M. Anderson, 37 Winding Way, Madison, N.J. 07940

[*] Notice: The portion of the term of this patent subsequent to Apr. 21, 2009 has been disclaimed.

[21] Appl. No.: 698,199

[22] Filed: May 6, 1991

Related U.S. Application Data

[63] Continuation of Ser. No. 437,184, Nov. 16, 1989, abandoned.

[51] Int. Cl.⁵ ............................................. A61B 19/00
[52] U.S. Cl. .................................. 128/899; 128/903; 604/362; 606/1
[58] Field of Search ............... 128/899, 903, 654, 631; 600/12, 13, 20; 606/1; 604/362

[56] References Cited

U.S. PATENT DOCUMENTS

| | | | |
|---|---|---|---|
| 4,114,601 | 9/1978 | Abels | 600/20 |
| 4,193,405 | 3/1980 | Abels | 604/362 |
| 4,196,734 | 4/1980 | Harris | 606/38 |
| 4,658,818 | 4/1987 | Miller, Jr. et al. | 606/1 |
| 4,719,919 | 1/1988 | Marchosky et al. | 128/401 |

Primary Examiner—William E. Kamm
Assistant Examiner—Kevin Pontius
Attorney, Agent, or Firm—Ernest D. Buff

[57] ABSTRACT

An apparatus for detecting a surgical implement in human or animal tissue has means for defining a transmitting zone encompassing a surgical wound in the tissue. A battery powered marker is secured to a surgical implement positioned within the wound. Field generating means are provided for generating within the transmitting zone an electromagnetic field having a predetermined frequency band. A signal generating means generates a signal having a predetermined frequency band. The signal generating means is operative to cause the field generating means to generate the electromagnetic field, providing the marker with signal identity. A detecting means having an antenna located within the transmitting zone of the marker detects the marker signal irrespective of the marker's orientation therewithin.

5 Claims, 8 Drawing Sheets

SURGICAL IMPLEMENT DETECTOR UTILIZING A POWERED MARKER

This application is a continuation of application Ser. No. 437,184 filed Nov. 16, 1989, now abandoned.

BACKGROUND OF THE INVENTION

1. Field of the Invention

The present invention relates to a method for detecting a marked surgical implement such as a sponge, clamp, or a catheter within a surgical wound in human or animal tissue irrespective of its position or orientation therewithin.

2. Description of the Prior Art

During the course of a surgical operation it is frequently necessary for articles, such as surgical sponges, gauzes, instruments, needles, and the like, to be placed into a wound cavity. Notwithstanding rigorous precautions attendant surgical procedures, such items are sometimes inadvertently lost during surgery and remain within the patient. When this happens, the patient can encounter serious consequences, including pain, infection, intestinal obstruction, and even death. The problem of retained surgical implements has existed since the earliest days of surgery. Procedures conventionally employed to prevent post-surgical implement retention include a manual search of the wound by the surgeon prior to closure and a careful accounting for all materials inserted and removed from the wound. The accounting function is customarily carried out by the operating room staff, usually the circulating nurse. Despite these precautionary measures the accidental retention of surgical implements continues to occur with disturbing regularity, even in prestigious institutions, and is regarded by surgeons as a major unsolved problem.

At present, manual search and physical count remain the primary methods used in detection of retained surgical implements. Most surgical instruments are composed of metal, and are easily detectable by x-ray. Sponges have been tagged with radiopaque markers to make them also visible on x-ray, but x-rays are not routinely done before completion of the operation because of several disadvantages including inconvenience, expense, loss of operative time, and radiation exposure. Postoperative x-rays suffer from some of the same disadvantages. Moreover, even when postoperative x-rays are taken, retained items are occasionally overlooked; but even if detected, require a second operation to effect their removal.

To overcome the difficulty of detecting retained surgical implements, it has been suggested that the implements be provided with a radioactive tracer. This technique, disclosed by U.S. Pat. No. 2,740,405 to Riordan, is subject to obvious hazards associated with use, storage and disposal of radioactive materials.

It has also been proposed that surgical sponges be marked with a flexible plastic impregnated with either paramagnetic or ferromagnetic materials in the form of powders. Detection of these marked sponges is accomplished by a metal detector. This method, taught by U.S. Pat. No. 3,422,816 to Robinson et al., provides very small signals difficult to detect over the width of a patient's body. In addition, the Robinson et al. technique provides no discrimination against other metal objects, such as staples which, though present within the surgical wound, are appointed for retention therewithin.

Yet another proposal, advanced by U.S. Pat. No. 3,587,583 to Greenberg, involves use of surgical sponges marked with magnetized particles whose presence is detectable with magnetodiodes. In practice, however, the magnetic field generated by these particles is too small to be readily detected by the diodes.

U.S. Pat. No. 4,114,601 to Ables discloses the use of a small transponder fixed to a surgical sponge or instrument. This transponder exhibits gyromagnetic resonance at preselected frequencies. Detection is accomplished by nonlinear mixing of two frequencies impinging upon the transponder. The gyromagnetic resonance effect disclosed by Ables is a high frequency phenomenon, existing at frequencies of the order of about 5 gigahertz (5,000,000,000 cycles/sec). These frequencies, known as microwaves, are absorbed readily by animal tissue and are, in fact, used in microwave ovens for cooking. In use of the Ables type transponder, the energy developed goes primarily into heating tissue, rather than exciting the transponder into gyromagnetic resonance.

SUMMARY OF THE INVENTION

The present invention provides a method and apparatus for accurately and reliably detecting surgical implements within animal or human tissue. The apparatus comprises a detector responsive to the presence, within a detection zone, of a surgical implement to which a marker is secured. The marker is adapted to produce identifying signal characteristics within the detection zone of the detector.

Generally stated the apparatus comprises means for defining a transmitting zone encompassing a surgical wound within human or animal tissue. A marker is secured to a surgical implement positioned within the wound, the marker being battery powered. The apparatus has a field generating means for generating an electromagnetic field having a predetermined frequency within the transmitting zone. A signal generating means is provided for generating a signal having a predetermined frequency band. The signal generating means is operative to cause the field generating means to generate the electromagnetic field, providing the marker with signal identity. A detecting means having an antenna located within the transmitting zone of the marker detects the marker signal irrespective of the marker's orientation therewithin.

More specifically, the marker comprises a miniature electronic transmitter enclosed within a water-tight case. The case is comprised of a plastic that remains inert to the body for the duration of the surgery. The transmitter is comprised of a battery and electronic circuit, and is adapted to provide a unique identifying signal. A detector placed within the transmitting zone of the marker is adapted, irrespective of the orientation of such marker, to detect the marker signal and record such detection with visual and/or audio indicators.

Advantageously, the method and apparatus of the invention detect retention of surgical implements with far greater accuracy than methods and means involving a physical count of implements that enter and exit the wound. The apparatus is inexpensive to construct, safer for the patient than postoperative X-rays and avoids risk to the environment posed by radioactive tracers. Generation of a strong signal is effected in a highly reliable manner. The signal is more easily distinguished than signals generated by magnetic detection systems, and is generated without the heating of tissue caused by microwave detection systems.

BRIEF DESCRIPTION OF THE DRAWINGS

The invention will be more fully understood and further advantages will become apparent when reference is made to the following detailed description of the preferred embodiment of the invention and the accompanying drawings in which.

DESCRIPTION OF THE PREFERRED EMBODIMENTS

Figure 1:
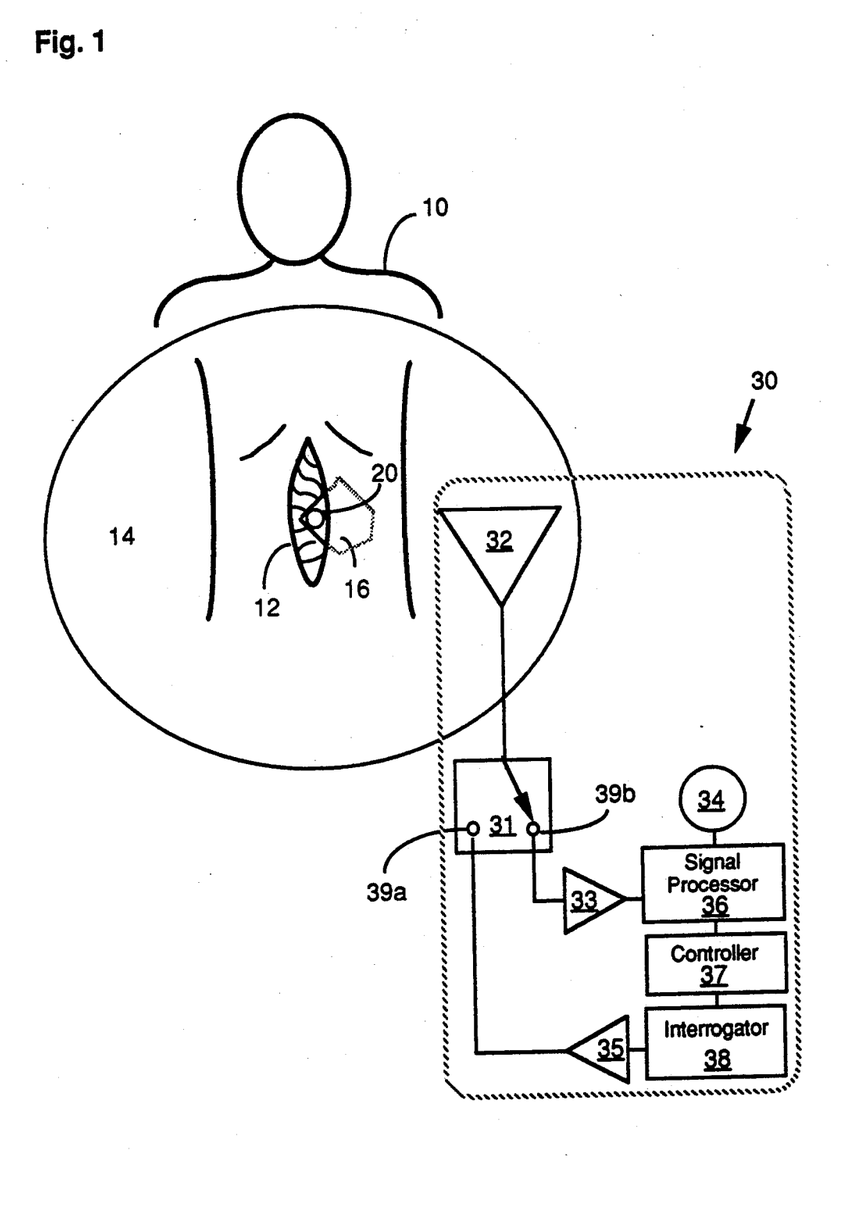
FIG. 1 is a block diagram of a surgical implement detector incorporating the present invention.
Figure 2:
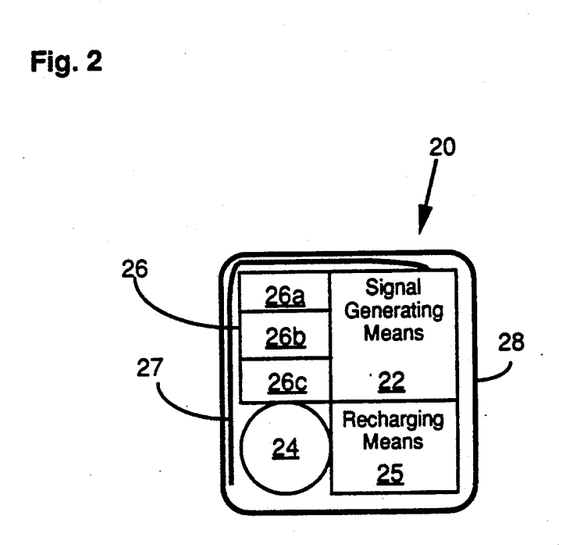
FIG. 2 is a block diagram of a marker suited for use in the detector of FIG. 1.
Figure 3:
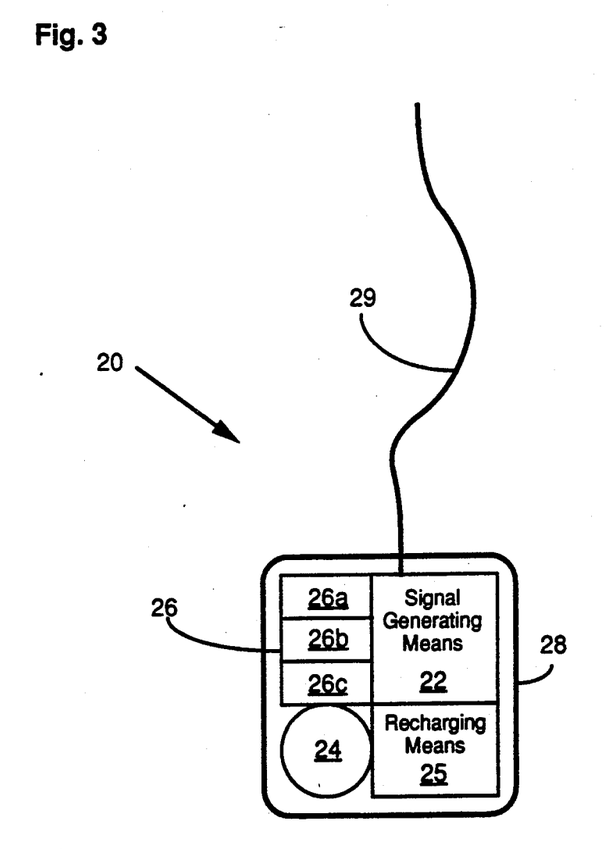
FIG. 3 is a block diagram of a marker having an external tail antenna.

Referring to the drawings, there is shown in FIG. 1 a block diagram of a surgical implement detector incorporating the present invention. A marker 20 is secured to a surgical implement 16, such as a sponge, positioned within the wound. The marker 20 has means for defining a transmitting zone 14 encompassing a surgical wound 12 within patient 10. The marker, shown generally at 20 in FIG. 2, consists of a case 28 comprised of a material, such as ABS plastic, that will remain inert within the wound for the period of the surgery. Within the case 28 is housed a signal generating means 22, a field generating means 27, a starting means 26, a power means 24, and a recharging means 25. The configuration of field generating means 27 depends on the frequency of the signal produced by the signal generating means 22. Below 3 megahertz the field generating means 27 typically consists of a loop antenna comprised of one or more turns of enamel coated wire. Above 3 megahertz the field generating means 27 typically comprises a single lead, 2" or less in length, wound within the case and attached at one end to the signal generating means 22. Alternatively, as shown in FIG. 3, antenna 29 can be lengthened and connected through the case as a tail, thus enlarging the transmitting zone 14. In this case, the antenna 29 outside the case 28 is comprised of flexible, insulated wire. Upon being activated by a signal from the detector, shown generally at 30, the starting means 26 causes the power means 24 to be connected to the signal generating means 22 which, in turn, is connected to the field generating means 27. The resulting field is transmitted within zone 14 for a predetermined period of time. The starting means 26 is comprised of a narrow band receiver 26a tuned to receive said signal from detector 30, a timing circuit 26b, and a switch 26c. Timing circuits are well known in the art and can be constructed from a type 555 timer, where a resistor and capacitor establish said predetermined time. Switch 26c is typically a simple transistor. The power means 24 is typically a rechargeable battery, such as NiCd, periodically refreshed by the recharging means 25. The recharging means 25 is comprised of a coil of wire connected to an ac to dc rectifier. An external ac source is inductively coupled via a coil to the coil in the recharging means 25. Alternatively, the recharging means 25 is comprised of two external contacts through the case 28. Recharging is accomplished by direct connection with an external dc source.

The detector 30 comprises an antenna 32, an electronic switch 31, a controller 37, an interrogator 38 and its amplifier 35, a signal processor 36 and its filtering preamplifier 33, and an indicator 34. The controller 37 acts as a common timing element for the processor 36, the interrogator 38, and the switch 31. The switch 31 connects the antenna 32 to either the processor preamp 33 or the interrogator amp 35 and contains the appropriate impedance matching elements for each connection.

Figure 8:
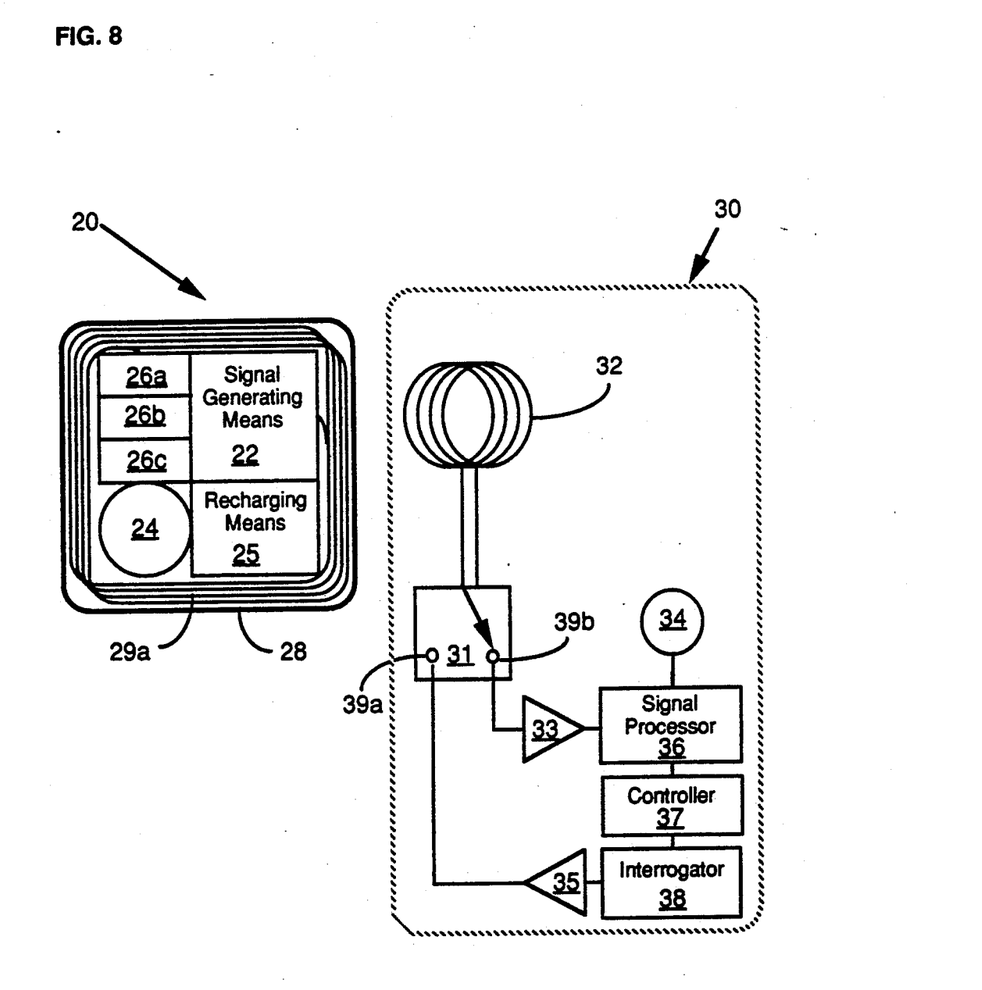
FIG. 8 is a block diagram of a surgical implement detector incorporating a coil antenna and a block diagram of a marker having a coil field generating means.

When activated by operating room personnel, the controller 37 causes the switch 31 to connect antenna 32 to position 39a. The controller next causes the interrogator 38 to generate a single signal burst or, alternatively, a periodic signal burst, enhanced by amplifier 35 and transmitted through switch 31 and antenna 32 to the marker 20, thereby activating the marker's starting means 26 as described above. The signal transmitted into zone 14 by the marker 20 is received by the detector 30 through its antenna 32, placed within zone 14. The controller next causes switch 31 to connect antenna 32 to position 39b. After filtering and amplification by preamp 33 and verification of the received signal by the processor 36, the indicator 34 is activated. The indicator is comprised of visual and/or aural transducers, such as a light and/or a buzzer. The configuration of the detector antenna 32 depends on the frequency of the marker signal, as does the marker's field generating means 27. Typically, below 3 megahertz the antenna 32 is a coil and above 3 megahertz it is typically a single-end lead or whip antenna. FIG. 8 depicts detector 30 having a coil antenna 32 for operation below 3 MHz and a marker 20 similarly provided with a coil field generating means 29a.

Alternatively, the power means 24 is not rechargeable but comprises an alkaline or lithium battery. The signal transmitted by the marker 20 is of sufficiently long duration, at least 1/f milliseconds where f is the frequency of transmission in kilohertz, to be detected by the detector 30. In this manner, power usage is minimized and battery life is maximized. The marker construction is simplified by elimination of the recharging means 25.

Figure 4:
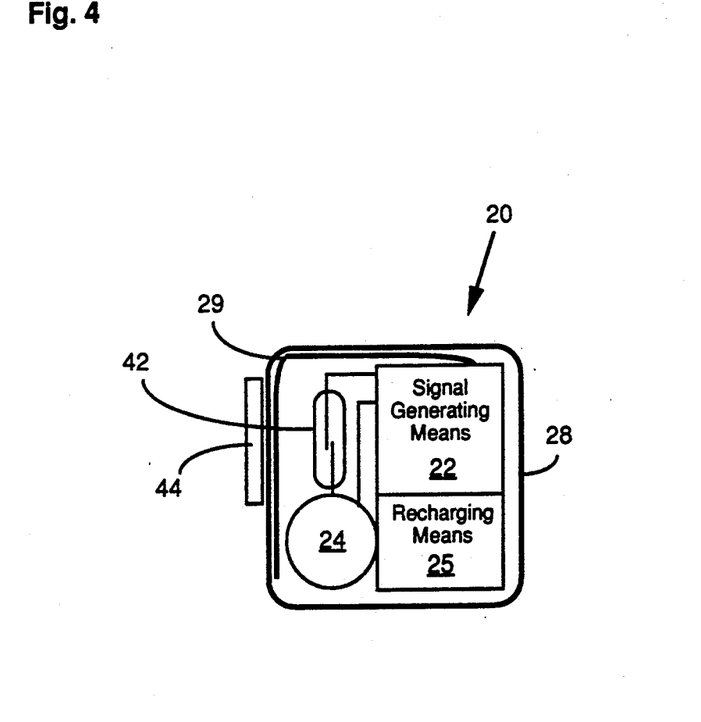
FIG. 4 is a diagram of a marker with a reed-switch starting means.

In a second embodiment of the invention, with reference to FIG. 4, switch 31, interrogator 38 and amplifier 35 of detector 30 are eliminated. With this embodiment, the starting means 26 of marker 20 must be manually activated by operating room personnel before the marked implement 16 is placed within the wound 12. Marker 20 is rechargeable or, alternatively, nonrechargeable as described in the previous embodiment. The starting means 26 is comprised of a normally-closed reed switch 42. A permanent magnet 44 placed on the outside of the case causes the switch 42 to be in the open position. Removing, demagnetizing, or reorienting magnet 44 by 90 degrees causes the switch 42 to close, thereby energizing the generating means 22. This, in turn, causes marker 20 to transmit a periodic signal. Detector 30, with the elimination of the interrogator 38, works as described in the previous embodiment. Replacing, remagnetizing or reorientating the magnet 44 causes switch 42 to open and marker 20 to cease transmitting.

Figure 5:
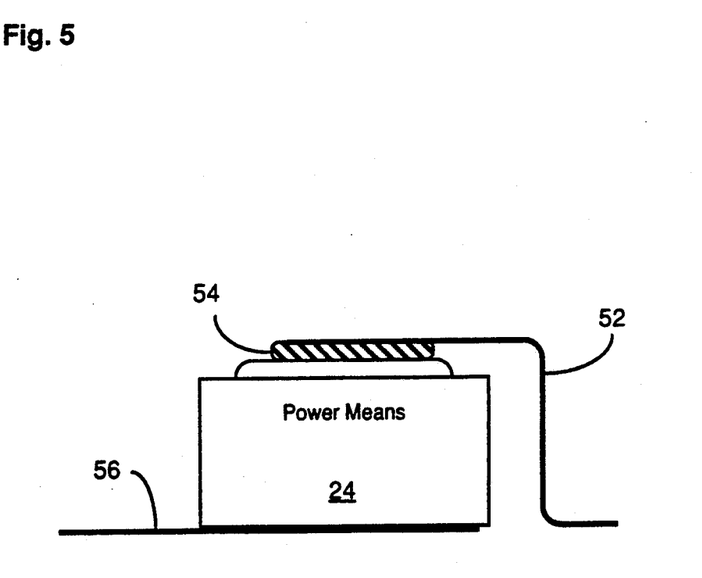
FIG. 5 is a side-view diagram of a wax-spacer starting means.
Figure 6:
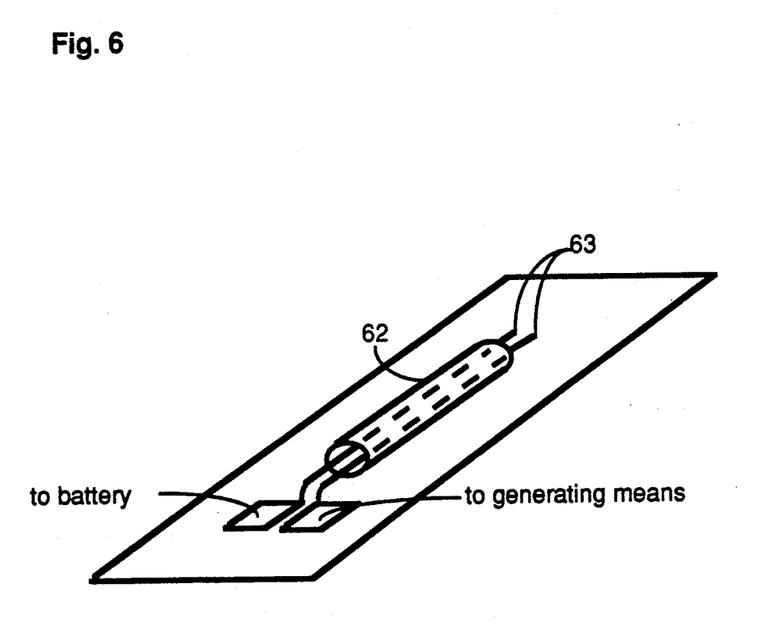
FIG. 6 is an isometric view of a shrink-tube starting means.

In a third embodiment of the invention, described with reference to FIG. 5, the starting means can be activated only once, the activation being accomplished by operating room staff prior to the marker's first use. The marker's power means 24 is nonrechargeable and the recharging means 25 is eliminated. The starting means 26 is heat-activated and it is comprised of a spring-loaded battery contact 52 and an insulating wax spacer 54. Alternatively, battery 24 is coated with wax 54, thereby electrically insulating battery contacts 52 and 56 from battery 24. The wax 54 is selected to have a melting point, preferably at the standard operating point of gas sterilizers, approximately 140 degrees Fahrenheit. Beeswax and paraffin meet this criterion. Melting of the wax 54 causes the spring-loaded or cantilevered contacts 52 and 56 to close against battery 24 energizing the generating means 22, whereby marker 20 transmits a periodic signal. Alternatively, as shown in FIG. 6, starting means 26 is comprised of a sleeve of heat-shrink tubing 62 placed around two cantilevered contacts 63. Heat-shrink tubing typically requires temperatures of 100 degrees centigrade to activate and cannot therefore be in low temperature gas sterilizers but must be activated by steam or boiling water baths. Heating causes tubing 62 to contract and close the two cantilevered contacts 63, causing marker 20 to transmit a periodic signal. Detector 30 works as described in the previous embodiment.

EXAMPLE I

Figure 7:
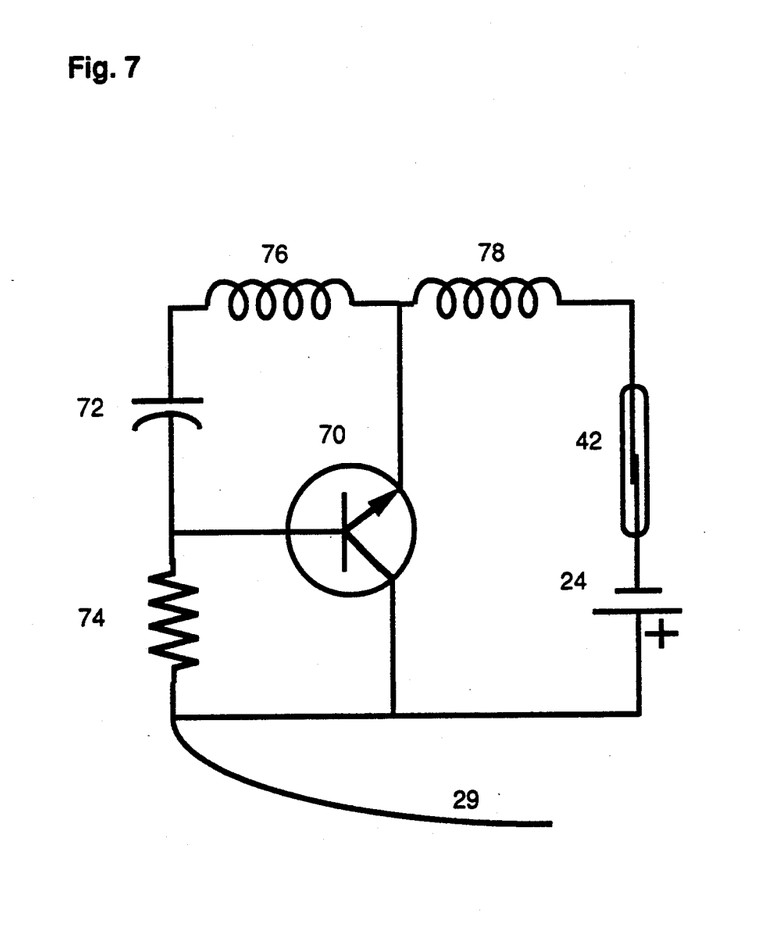
FIG. 7 is a schematic electrical circuit of a nonrechargeable marker.

To further illustrate the present invention, a marker was constructed using the circuit shown in FIG. 7. Numerous other circuit configurations are viable, but the circuit specified in FIG. 7 was chosen for its simplicity. Inductors 76 and 78 were constructed as ¼ inch diameter by approximately ½ inch length air-core coils each comprised of 10 turns of 24 gauge magnet wire. Resistor 74 was 200K ohms and capacitor 72 was a 10 mfd Tantalum. NPN transistor 70 was 2N2222. Battery 24 was a 1.5 V button type EP675 and reed switch 42 was a normally closed type. The circuit was placed on a ¾ inch diameter mounting board and housed within a water-tight case having a threaded lid. No antenna lead was used. A 1 inch bar magnet placed outside the case but parallel to reed switch 42 was sufficient to open switch 42 causing the marker to be inactive. On removing the magnet, switch 42 closes, causing marker 20 to emit a broad frequency signal having a range from about 15 MHz to 30 MHz and modulated at approximately 1 Hz. The signal was received by an ordinary shortwave radio in the aforesaid frequency range at up to 10 feet with all orientations of the marker 20, even when the marker 20 was surrounded on all sides by at least 9 inches of water.

EXAMPLE II

The procedure of Example I was repeated except that the marker used was provided with a 3 inch tail antenna as illustrated in FIG. 3. The marker's transmit zone 14 increased by approximately 50%.

EXAMPLE III

A marker was placed within a human cadaver. The marker used had the construction described in Example I, except that the starting means 26 was comprised of two contacts manually closed causing marker 20 to emit a broad frequency signal having a range from about 15 MHz to 30 MHz and modulated at approximately 1 Hz. The detector comprised an ordinary shortwave radio with an insulated wire monopole antenna placed on the operating table along side the body. All orientations of the marker were detected.

Having thus described the invention in rather full detail, it will be understood that such detail need not be strictly adhered to but that various changes and modifications may suggest themselves to one skilled in the art, all falling within the scope of the invention as defined by the subjoining claims.

What is claimed is:

1. An apparatus for detecting a surgical implement in human or animal tissue, comprising:
    (a) a marker secured to a surgical implement positioned within a surgical wound, said marker being battery powered and including a starting means having a receiver means for receiving a first signal and a switch connected to said battery and associated with a timing means for activating said marker for a predetermined period of time;
    (b) field generating means for transmitting an electromagnetic field having a predetermined frequency band;
    (c) signal generating means activated by said starting means in response to receipt of a first signal to cause said field generating means to transmit said electromagnetic field for said predetermined period of time, said electromagnetic field being a second signal that provides said marker with signal identity, said predetermined period of time being about 1/f milliseconds, where "f" represents frequency of transmission in kilohertz, and said starting means operating in response to said first signal to close said switch, connecting said signal generating means with said battery;
    (d) detection means having (i) an interrogator means for generating and transmitting said first signal to said starting means, (ii) a signal processor means for receiving said second signal and (iii) an antenna, said antenna being alternately connected to said interrogator and said signal processor for generating said first signal and receiving said second signal to detect said marker;
    (e) said field generating means consisting of a coil when said second signal has a frequency below 3 megahertz and comprising a single end lead when said second signal has a frequency above 3 megahertz; and
    (f) said antenna being a coil when said second signal has a frequency below 3 megahertz and comprising a single end lead when said second signal has a frequency above 3 megahertz.

2. An apparatus as recited in claim 1, wherein said signal processor detects and verifies said activation of said marker.

3. An apparatus as recited in claim 2, wherein said detection means further comprises a switch for connecting said antenna to either of said signal processor and said interrogator.

4. An apparatus as recited in claim 1, wherein said detection means further includes an indicating means for providing an audible or visible alarm when said marker is activated.

5. A method for detecting a surgical implement in human or animal tissue, comprising the steps of:

(a) attaching a marker to a surgical implement appointed for disposition within a surgical wound, the marker being battery powered;
(b) transmitting an electromagnetic field upon receipt of a first signal, said electromagnetic field having a predetermined frequency band;
(c) generating said first signal to initiate transmission of said electromagnetic field for a predetermined period of time, said electromagnetic field being a second signal that provides said marker with signal identity and said predetermined period of time being about 1/f milliseconds, where "f" represents frequency of transmission in kilohertz; and
(d) receiving said second signal to detect said marker.

* * * * *